United States Patent [19]

Maier

[11] 4,160,779
[45] Jul. 10, 1979

[54] PROCESS FOR THE PRODUCTION OF METHYLAMINOMETHYLPHOSPHONIC ACID AND ITS SALTS

[75] Inventor: Ludwig Maier, Arlesheim, Switzerland

[73] Assignee: Ciba-Geigy Corporation, Ardsley, N.Y.

[21] Appl. No.: 949,829

[22] Filed: Oct. 10, 1978

[30] Foreign Application Priority Data

Oct. 12, 1977 [CH] Switzerland ............... 12455/77

[51] Int. Cl.² .................................................. C07F 9/38
[52] U.S. Cl. ............................. 260/502.5; 260/501.12
[58] Field of Search .................................... 260/502.5

[56] References Cited

U.S. PATENT DOCUMENTS 3,160,632  12/1964  Toy et al. ........................ 260/502.5

3,776,953  12/1973  Maier ............................. 260/502.4 R

OTHER PUBLICATIONS

Il'ina et al., "Izv. Akad. Nauk. SSSR", 1968, vol. 8, pp. 1860–1862.

*Primary Examiner*—Joseph E. Evans
*Attorney, Agent, or Firm*—Harry Falber

[57] ABSTRACT

A process for the production of methylaminomethylphosphonic acid of the formula

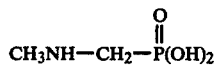

and salts thereof is given. It consists in reacting bis(chloromethyl)phosphonic acid in aqueous medium with ammonia at elevated temperature under pressure.

3 Claims, No Drawings

PROCESS FOR THE PRODUCTION OF METHYLAMINOMETHYLPHOSPHONIC ACID AND ITS SALTS

The present invention provides a novel process for the production of methylaminomethylphosphonic acid and its salts. Eligible salts are in particular those of bases, such as the ammonium salts, alkali metal and alkaline earth metal salts and salts of organic (alkyl)amines.

It has recently been found that the known methylaminomethyl-phosphonic acid of the formula I

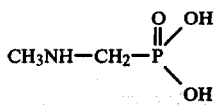  (I)

has interesting herbicidal properties which lend added importance to this compound. Up till now, it has only been possible to prepare this known compound by relatively complicated methods.

According to the teaching of U.S. Pat. specification No. 2,328,358, the N-methyl-N-hydroxymethylstearamide of the formula

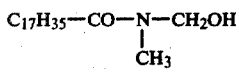

is reacted with PCl$_3$ to give the corresponding phosphonic dichloride, which, after treatment with dilute hydrochloric acid, affords the corresponding amidophosphonic acid

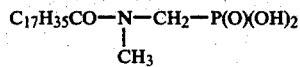

which is then saponified to produce the methylaminomethylphosphonic acid.

The very lengthy reaction times constitute a severe drawback of this process.

In another known process (disclosed in U.S. Pat. specification No. 3,907,652), the N-tertiary aminomethylphosphonic acid of the formula

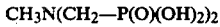

is prepared initially by a Mannich reaction of methylamine, formaldehyde and phosphorous acid (H$_3$PO$_3$) [Journ. Org. Chem. 31, 1603 (1966)] and subsequently oxidised by electrolysis to CH$_3$NH—CH$_2$—P(O)(OH)$_2$ with removal of a phosphonomethyl group.

Attempts to produce monomethylaminomethylphosphonic acid via its esters by reaction of formaldehyde, methylamine and dialkyl phosphites (diesters of phosphorous acid), that is to say, using a lower primary amine, have hitherto failed on account of secondary reactions and of the strong tendency of the formaldimine intermediates to polymerise (E. K. Fields, J. Am. Soc. 74, 1528 (1952). On the other hand, it is stated in this reference that this method can be employed for the production of dialkylaminomethylphosphonic acid esters from secondary amines.

Very surprisingly, a novel process for the direct production of methylaminomethylphosphonic acid, CH$_3$NH—CH$_2$—P(O)(OH)$_2$, has now been found, which is based on an unexpected reaction mechanism.

The novel process comprises reacting bis(chloromethyl) phosphinic acid

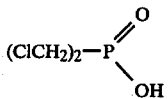

in water or in an aqueous medium, with ammonia at elevated temperature and under pressure. Bis(chloromethyl)phosphinic acid is a known compound ("Organic Phosphorus Compounds", ed. G. M. Kosolapoff and L. Maier, John Wiley, New York 1972, Vol. 6, page 82).

The surprising feature of the reaction of the present invention is that a phosphinic acid is formed from a phosphinic acid.

The procedure to be followed is advantageously that a mixture of bis(chloromethyl)phosphinic acid, water or water/alcohol and at least three times the molar amount of ammonia, is heated under pressure, preferably in an autoclave, to 100°–200° C., preferably to about 150° C. The pressure during the reaction rises to 70 to 100 bar, on average to about 80 bar. After a reaction time of several hours (about 5 to 8 hours), the brown solution is filtered and made alkaline with sodium hydroxide solution in order to remove ammonium chloride.

The desired methylaminomethylphosphonic acid is obtained in the form of its sodium salt by evaporation of the alkaline solution. The free acid with a melting point of 270°–274° C. (with decomp.) can be obtained from the salt in conventional manner by acidification or by passing the aqueous solution of the sodium salt over an acid ion exchanger.

It must be presumed that, in the reaction mechanism of this surprising reaction, a four-membered ring intermediate is formed, which is hydrolyzed into the phosphonic acid by water, and that consequently the reaction proceeds in accordance with the following scheme:

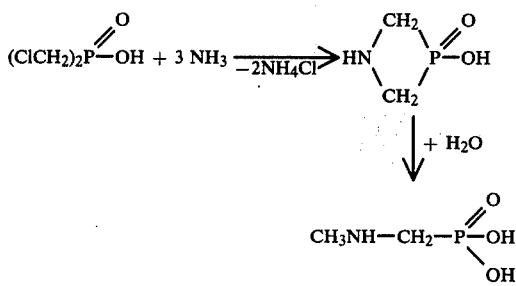

This reaction mechanism also seems to play a minor part in the reaction of aliphatic primary amines with bis(chloromethyl)phosphinic acid, where it occurs as a troublesome secondary reaction. It has been observed by the applicant for example that, in the reaction of bis (chloromethyl)-phosphinic acid with tert-butylamine in accordance with M. K. Il'ina and I. M. Shermergorn, Bull. Acad. Sci. USSR, 1968, page 1759 (English edition), not only is the desired bis(tert-butylaminomethyl)phosphinic acid described in this reference obtained in 30.4% yield, but also small amounts (3.2%) of tert-butyl-methylaminomethylphosphonic acid of the formula

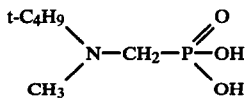

simultaneously result. Likewise, in the reaction of bis(chloromethyl)phosphinic acid with methylamine, a small amount of dimethylaminomethylphosphonic acid

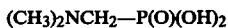

is formed in addition to the expected bis(methylaminomethyl)-phosphinic acid.

The following Example will serve to illustrate the process of the present invention in more detail.

EXAMPLE

A mixture of 32.6 g (0.2 mole) of bis(chloromethyl)-phosphinic acid, $(ClCH_2)_2P(O)OH$, 200 ml of water and 300 g of ammonia is heated in an autoclave for 7 hours to 150° C., whereupon the pressure rises to 80 bar.

A brown solution is obtained, which is filtered. To remove ammonium chloride, sodium hydroxide is added until the onset of alkaline reaction. The alkaline solution is then evaporated to dryness, affording as residue the sodium salt of the desired methylaminomethylphosphonic acid. The free acid is obtained by dissolving the residue in a small amount of water and passing the solution over an acid ion exchanger. Evaporation of the eluate yields the pure acid

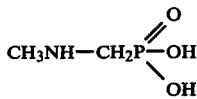

with a melting point of 270°–274° C. (with decomp.).

$^1$H-NMR (in $D_2O$): $CH_3$ 2.82 ppm (s, 3H); $PCH_2$ 3.23 ppm (d, $J_{PCH}$13Hz, 2H); NH,OH 4.8 ppm $^{31}$P-chemical shift in $D_2O$:–9.2 ppm.

Reaction of the methylaminomethylphosphic acid with tertbutylamine produces the crystalline mono-salt with a melting point of 261°–267° C. (with decomp.). The correspondingly obtained isopropylamine mono-salt melts at 268°–271° C. (with decomp.).

What is claimed is:

1. A process for the production of methylaminomethylphosphonic acid of the formula

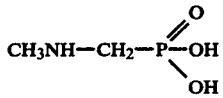

and the salts thereof, which comprises reacting bis(chloromethyl) phosphinic acid

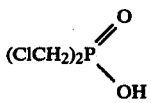

in water or an aqueous medium, with ammonia at 100°–200° C. and under autogenous pressure, and isolating the methylaminomethylphosphonic acid from the reaction mixture in the form of the free acid or of a salt.

2. A process according to claim 1, wherein a mixture of bis(chloromethyl)phosphinic acid and aqueous ammonia is heated in an autoclave for several hours to about 150° C.

3. A process according to claims 1 or 2, wherein ammonium chloride formed in the reaction mixture is decomposed by addition of sodium hydroxide solution and the sodium salt of methylaminomethylphosphonic acid is isolated by evaporation of the alkaline solution.

* * * * *